United States Patent [19]
Gotanda et al.

[11] Patent Number: 5,387,190
[45] Date of Patent: Feb. 7, 1995

[54] PROBE BREAK DETECTOR FOR AN ULTRASONIC ASPIRATOR

[75] Inventors: Masakazu Gotanda, Sagamihara; Tatsuya Kubota, Machida; Tetsumaru Kubota; Yuichi Ikeda, both of Hachioji; Toshihiko Hashiguchi, Sagamihara; Hitoshi Karasawa, Hachioji; Tadao Hagino, Yokohama, all of Japan

[73] Assignee: Olympus Optical Co., Ltd., Tokyo, Japan

[21] Appl. No.: 228,005

[22] Filed: Apr. 15, 1994

Related U.S. Application Data

[63] Continuation of Ser. No. 829,575, Feb. 3, 1992, abandoned, which is a continuation of Ser. No. 713,025, Jun. 7, 1991, abandoned, which is a continuation of Ser. No. 265,630, Nov. 1, 1988, abandoned.

[30] Foreign Application Priority Data

Dec. 9, 1987 [JP] Japan .................. 62-312665
Aug. 3, 1988 [JP] Japan .................. 63-194001

[51] Int. Cl.6 .............................................. A61B 17/36
[52] U.S. Cl. .......................................... 604/22; 601/2; 606/1; 606/169

[58] Field of Search .................. 340/540, 635, 652; 200/61.08; 604/22; 601/2; 310/314, 317; 606/1, 169; 408/12

[56] References Cited

U.S. PATENT DOCUMENTS 4,118,139 10/1978 Lemelson ............................ 408/12

FOREIGN PATENT DOCUMENTS 49-83398 8/1974 Japan .
50-40089 4/1975 Japan .
WO87/01276 3/1987 WIPO .

*Primary Examiner*—David M. Shay
*Attorney, Agent, or Firm*—Armstrong, Westerman, Hattori, McLeland & Naughton

[57] ABSTRACT

An ultrasonic aspirator has a probe having the inside path made an aspirating path by being provided on the base side with an ultrasonic vibrator. The probe is used as an ultrasonic vibration transmitting member and is in contact at the tip with an object within a body cavity to crush the object and to discharge the crushed object out of the probe through the aspirating path. A device, for detecting a break of the probe, is provided so that, when the probe breaks, the vibration of the above mentioned ultrasonic vibrator will be stopped by a signal from the detecting device.

11 Claims, 5 Drawing Sheets

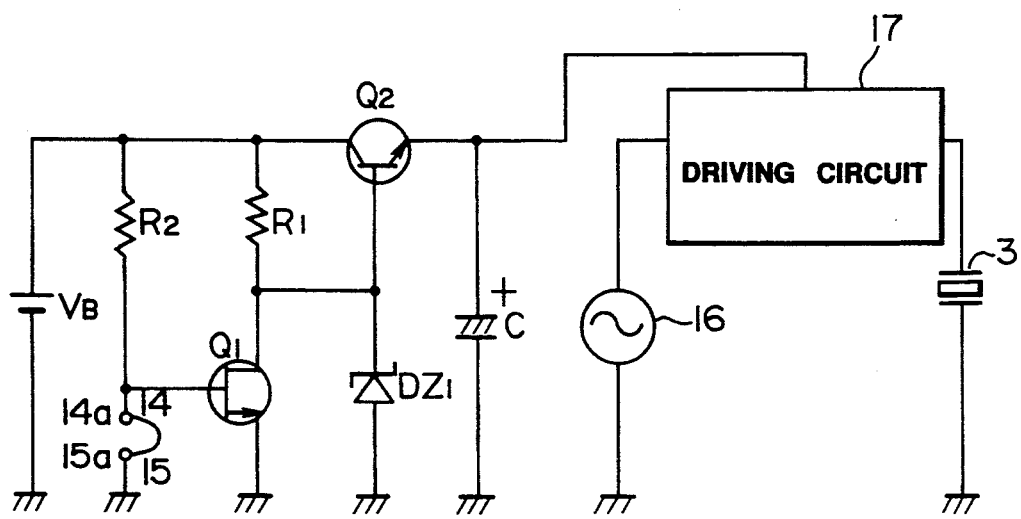
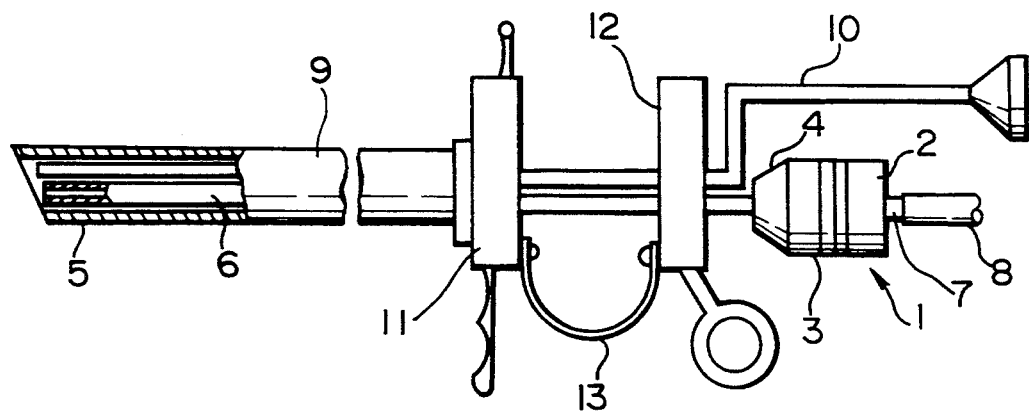

FIG. 2(a)
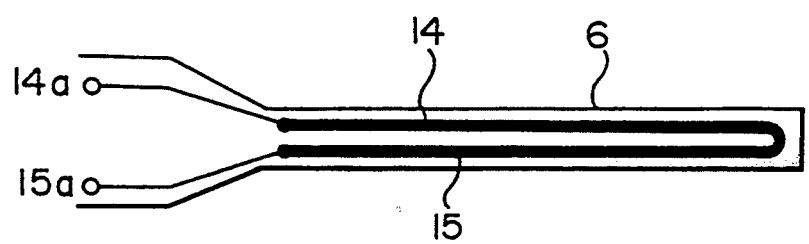
FIG. 2(b)
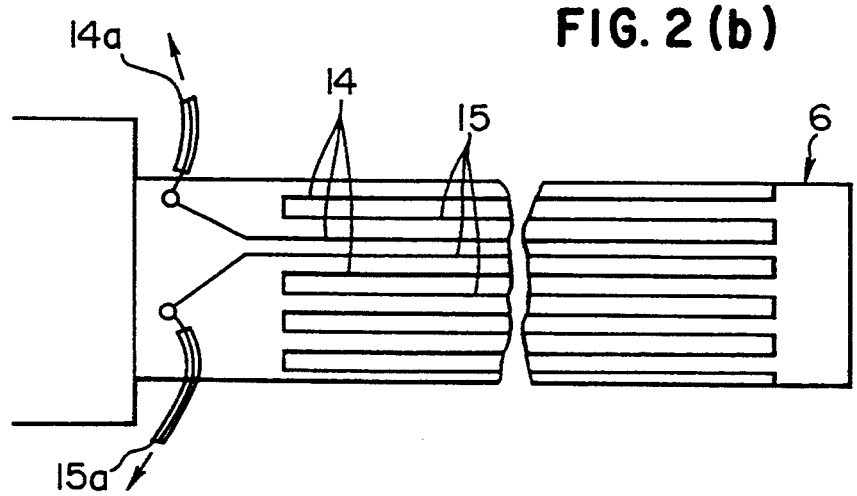
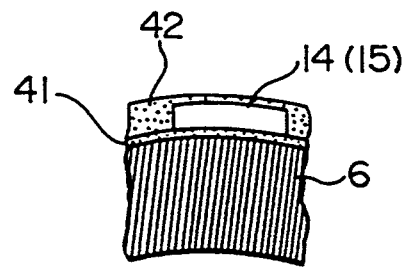
FIG. 2(c)

PROBE BREAK DETECTOR FOR AN ULTRASONIC ASPIRATOR

This application is a continuation of application Ser. No. 07/829.575 filed Feb. 3, 1992, now abandoned, which is a continuation of 07/713,025, filed Jun. 7, 1991, now abandoned, which is a continuation of 07/265,630, filed Nov. 1, 1988, now abandoned.

BACKGROUND OF THE INVENTION

Field of the Invention

This invention relates to an ultrasonic sucking apparatus of aspiration whereby a break of a pipe-like probe, transmitting an ultrasonic vibration, is detected and an ultrasonic oscillating device is controlled by the detected signal.

Related Art Statement

Recently, an extensively used endoscope, in medical and industrial fields, has through an observing optical -system and illuminating optical system provided in an elongate insertable part, an eyepiece part or the like on the base side. An affected part within a body cavity or the like in which the above mentioned insertable part is inserted, can be diagnosed or inspected or various treatments can be made by inserting treating tools.

In PCT WO 87/01276 an ultrasonic aspirator crushes a blood colt or tumor generated within a body cavity with ultrasonic waves and the crushed clot or tumor is aspirated to be removed out of the body cavity.

In this kind of ultrasonic aspirator, a probe, provided on the base side with an ultrasonic vibrator and having the inside path made an aspirator path, is used as an ultrasonic vibration transmitting member and is in contact at the tip with an object within a body cavity to crush the object and, to discharge the crushed object through the aspirating path within the probe.

The above mentioned probe, as an ultrasonic vibration transmitting member, may break during its ultrasonic vibration as inserted within a body cavity through a sheath. In such a case, if the transmission of the vibration is continued, it will be likely that the tissues within the body cavity will be hurt or the broken pieces will drop into the body cavity.

OBJECT AND SUMMARY OF THE INVENTION

An object of the present invention is to provide an ultrasonic aspirator whereby a break of a pipe-like probe, which transmits an ultrasonic vibration, is detected. An ultrasonic oscillating drive is controlled by the detected signal so that, as soon as the probe is broken, the ultrasonic vibration will be stopped to prevent tissues within a body cavity from being hurt and to prevent the broken pieces from dropping into the body cavity.

The ultrasonic aspirator of the present invention is provided with a probe which is provided on the base side with an ultrasonic vibrator and. The inside path of the probe is made an aspirating path. A detecting device detects a break of the probe so that an ultrasonic oscillating drive may be controlled by the detecting signal of this detecting. When the probe breaks, the break will be detected by the detecting device. The detected signal will be output and the ultrasonic oscillating drive will be controlled.

The other features and advantages of the present invention will become apparent with the following explanation.

BRIEF DESCRIPTION OF THE DRAWINGS

FIGS. 1 to 3 relate to the first embodiment of the ultrasonic aspirator of the present invention.

FIG. 1 shows an ultrasonic vibrator control circuit.

FIG. 2(a) is a first type of schematic view showing a probe construction.

FIG. 2(b) is a schematic view of a second type of probe construction.

FIG. 2(c) shows a cross-section of a portion of the probe according to either FIG. 2(a) or 2(b).

FIG. 3 is a partly sectioned side view showing an endoscope apparatus as an example using an ultrasonic aspirator.

FIG. 5 is a control circuit diagram.

FIG. 6 is a waveform diagram.

DETAILED DESCRIPTION OF THE PREFERRED EMBODIMENTS

Figure 4:
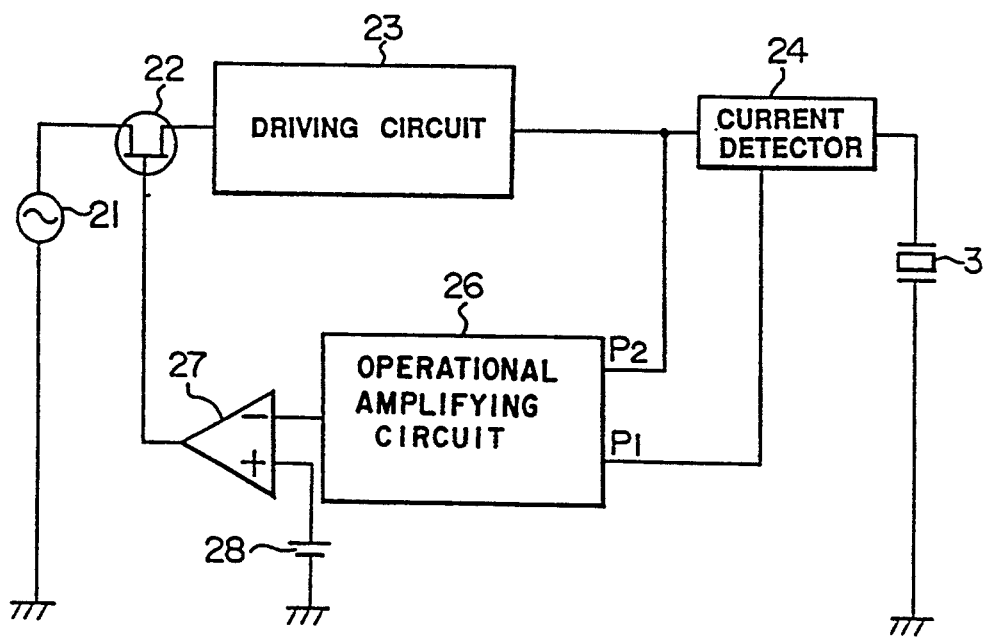
FIG. 4 is a circuit diagram of an ultrasonic vibrator control showing the second embodiment of the present invention.

In FIG. 3, the reference numeral 1 represents an ultrasonic aspirator wherein a piezoelectric vibrator 3 as an ultrasonic vibrator is arranged on the front surface of a base side body 2. A horn 4 is fitted on the front surface of this piezoelectric vibrator 3. A pipe-like probe 6, as an elongate ultrasonic vibration transmitting member having the inside path made an aspirating path 5, is extended forward of this horn 4. A aspirating path communicating with the sucking path 5 of this probe 6 is formed through the horn 4, piezoelectric vibrator 3 and body 2. An aspirating mouthpiece 7 is provided to project at the rear end of the body 2. An aspirating tube 8 connected to an aspirator (not illustrated) is connected to this mouthpiece 7. This ultrasonic aspirator 1 is used as inserted and assembled in a sheath 9 forming an endoscope apparatus as an example shown in FIG. 3. An optical sighting tube 10 is also to be inserted and assembled in this sheath 9. This sheath 9 has a handle part 11 and slider 12 in the base part. This slider 12 is energized rearward of the handle part 11 by a spring 13. When the slider 12 is slid forward against the energizing force of this spring 13, the probe 6 will be projected at the tip out of the sheath 9 at the tip opening so as to be able to contact an object tissue within the body cavity. The endoscope apparatus shown in FIG. 3 is an example. The ultrasonic aspirator 1 is used as combined with various endoscope apparatuses.

In this embodiment, as shown in FIG. 2(a), electrodes 14 and 15 as a break detecting means are formed, for example, by a plating means in the axial direction of the probe 6 so that, when the probe breaks, the electrodes 14 and 15 will break. Electrode terminals 14a and 15a are provided. These electrodes 14 and 15 and their terminals 14a and 15a are arranged in the circuit shown in FIG. 1.

In the example shown in the above mentioned FIG. 2(a), the electrodes 14 and 15 are wired only in a single pair in the form of a U in the axial direction of the probe 6 but, as shown in FIG. 2 (b), the above mentioned electrodes 14 and 15 may be wired in a plurality of pairs each in the form of a U in the axial direction over the entire periphery of the probe 6 at a fine pitch between the electrodes 14 and 15. When the electrodes 14 and 15 are closely wired in the probe 6 as shown in FIG. 2(b), even if the probe 6 breaks in a minute part, the break will be able to be detected.

In either of the examples in FIGS. 2(a) and 2(b), as shown in FIG. 2(c), the wired electrodes 14 and 15 are in close contact with the outer periphery of the probe 6 through a thin insulating layer 41 and are also coated on the surface with insulating layer 42 so that the probe 6 may not be irregular on the surface.

In the ultrasonic vibrator control circuit shown in FIG. 1, the reference symbol $V_B$ represents a direct current voltage source. A transistor $Q_2$, Zener diode $DZ_1$ resistance $R_1$ and condenser C form a stabilizing current source circuit which stabilizes the output voltage from the direct current voltage source $V_B$. That is to say, the output end of the direct current voltage source $V_B$ is connected to the collector of the transistor $Q_2$, the Zener diode $DZ_1$ is connected between the base of the transistor $Q_2$ and a reference potential point and the condenser C is connected between the emitter of the transistor $Q_2$ and a reference voltage point. The resistance $R_1$ is connected between the collector and base of the transistor $Q_2$. A resistance $R_2$ and a series circuit of the contacts 14a and 15a of the above mentioned electrodes 14 and 15 are connected between the collector of the transistor $Q_2$ and the reference potential point. The connecting point of the resistance $R_2$ and electrode contacts 14a and 15a is connected to the gate of an electrode field effect transistor $Q_1$ whose drain is connected to the base of the above mentioned transistor $Q_2$. The source of the electric field effect transistor $Q_1$ is connected to the reference potential point. The output voltage of the above mentioned stabilizing current source circuit is fed to a driving circuit 17 as a current source voltage of an oscillator consisting of an oscillator 16, the driving circuit 17 and piezoelectric vibrator 3.

In this formation, in the normal state when the probe 6 is not broken, the electric field effect transistor $Q_1$ will be off, the transistor $Q_2$ will be on, the output voltage of the stabilizing current source circuit will be fed to the driving circuit 17, the piezoelectric vibrator 3 will ultrasonically vibrate and the vibration will be transmitted to the probe 6 through the horn 4.

On the other hand, when the probe 6 breaks, the circuit between the contacts 14a and 15a will open. As a result, the electric field effect transistor $Q_1$ will be on, the transistor $Q_2$ will be off, the current source voltage of the stabilizing current source circuit will not be fed to the driving circuit 17 and the vibration of the piezoelectric vibrator 3 will stop. Therefore, when the probe 6 breaks, the ultrasonic vibration of the probe 6 will stop, the tissue within the body cavity will be prevented from being damaged by the vibration of the broken probe and the probe 6 will be prevented from dropping from the sheath 9.

FIG. 4 is a circuit diagram showing the second embodiment of the ultrasonic aspirator of the present invention.

In this embodiment, the drain and source of an electric field effect transistor 22 are connected between an oscillator 21 and driving circuit 23. A current detector 24 is connected between the driving circuit 23 and piezoelectric vibrator 3. The current detector 24 is a circuit detecting an alternating current flowing through the piezoelectric vibrator 3. The detected output current I of the current detector 24 is led to one input end $P_1$ of an operational amplifying circuit 26. The operational amplifying circuit 26 is input at the other input end $P_2$ with an output signal V from the driving circuit 23 and generates a voltage corresponding to the size of the current detected by the current detector 24. The output from the operational amplifying circuit 26 is input to the inverted input end of a comparator 27. The non-inverted input end of the comparator 27 is connected with a comparing voltage source 28. The output of the comparator 27 is fed to the gate of the transistor 22.

In the operation of this formation, in order that the output of the oscillator 21 may be input to the driving circuit 23, the output voltage of the operational amplifying circuit 26 is set to be of a voltage value smaller than the output voltage of the voltage source 28. Thus, normally when the probe 6 is not broken, the output voltage of the comparator 27 will present a high level, the electric field transistor 22 will be on and the piezoelectric vibrator 3 will be able to be driven.

When the probe 6 fitted to the piezoelectric vibrator 3 breaks, the impedance of the piezoelectric vibrator 3 will become so large that the current detected from the current detector 24 will become small. Therefore, the current input to one input end $P_1$ of the operational amplifying circuit 26 will become small, the voltage at the end $P_1$ will be reduced, its difference from the voltage at the other input end $P_2$ will become large (if the signal level flowing to the end $P_2$ of the operational amplifying circuit 26 from the driving circuit 23 is assumed to be constant). The output voltage of the operational amplifying circuit 26 will therefor become higher than the voltage from the voltage source 28. The output of the comparator 27 will be reduced to a low level and the electric field effect transistor 22 will be turned off. When the electric field transistor 22 is off, the signal from the oscillator 21 will be no longer input to the driving circuit 23 and the drive of the piezoelectric vibrator 3 will stop.

In a first modification of this embodiment, when the phase difference between the applied voltage and current is compared and is found to be above a certain value, the probe will be detected to be broken. For this modification, the reference numeral 26 in FIG. 4 represents a phase comparator and 27 represents a voltage comparator.

As a second modification of this embodiment, the impedance is detected to see whether the probe is broken or not by the size of the impedance. In this second modification, in FIG. 4, the reference numeral 26 represents a divider, one input end is represented by $\dot{\mathrm{i}}$ (instead of $P_1$), the other input end is represented by $\dot{\mathrm{E}}$ (instead of $P_2$). The impedance is detected by the formula $\dot{\mathrm{E}}/\dot{\mathrm{I}} = \dot{\mathrm{Z}}$ (impedance) and reference numeral 27 represents a voltage comparator.

In starting the drive of the vibrator 3, first of all, a minute the amount electric power is applied to the vibrator 3, the impedance, voltage or current phase difference of the vibrator 3 is checked. When the phase difference is within a predetermined value and, the probe is not broken, then a large amount of electric power is applied to drive the vibrator. When the above mentioned phase difference is above a predetermined value, the probe output will be abnormal and therefore the output to the vibrator 3 will be stopped.

Figure 5:
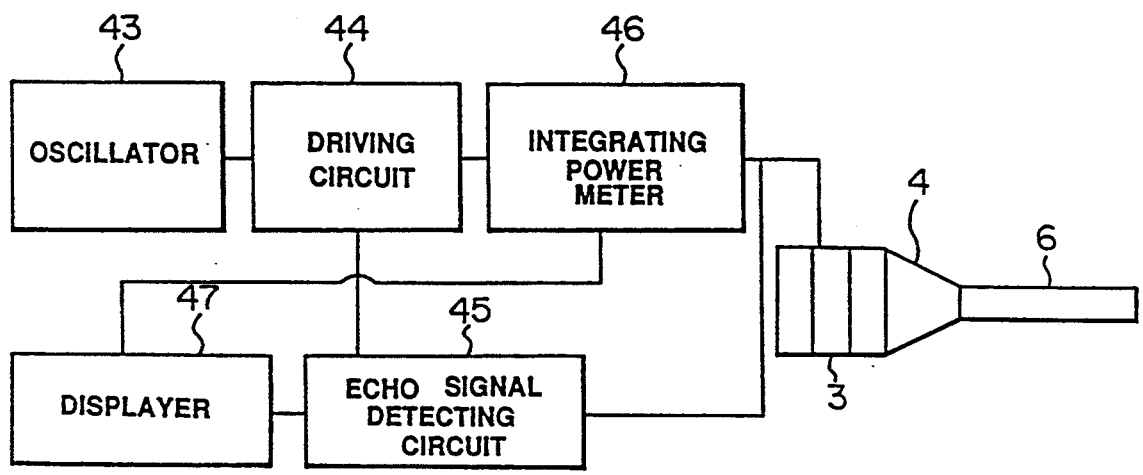
FIGS. 5 and 6 relate to the third embodiment of the present invention.
Figure 6:

FIGS. 5 and 6 are circuit diagrams showing the third embodiment of the ultrasonic aspirator of the present invention.

In this embodiment, an echo signal detecting circuit 45, integrating electric power meter 46 and a displayer 47, such as a CRT, are connected to an oscillator comprising an oscillator 43, driving circuit 44 and piezoelectric vibrator 3 (provided in a probe 6 through a horn 4).

In the above mentioned echo signal detecting circuit 45, the output end of the driving circuit 44 is connected to one input end and the piezoelectric vibrator 3, is connected to the other end so that an electric signal, to which an ultrasonic echo received by the piezoelectric vibrator is connected, may be input. The integrating electric power meter 46, integrating a driving electric power to the piezoelectric vibrator 3 is connected between the driving circuit 44 and piezoelectric vibrator 3. The output end of the integrating electric power meter 46 and the output end of the above mentioned echo Signal detecting circuit are connected to the displayer 47.

In this formation, before the drive of the piezoelectric vibrator is started, an impulse such as is shown in FIG. 6 is applied to the piezoelectric vibrator 3. An ultrasonic echo reflected from the probe 6 is converted into an electric signal by the piezoelectric vibrator 3. The echo signal is detected by the echo signal detecting circuit 45 and is displayed on the displayer 47. In case a defect such as hurting the patient's tissue or a break in the probe 6, the echo signal will be different. That is to say, if the tissue is hurt or the like, an echo signal will be generated at the position of the problem. When the probe 6 is found to be abnormal by the above mentioned echo signal, the drive of the driving circuit 44 will be stopped. The position and shape of the defect of the probe 6 can be displayed on the displayer 47. In the above mentioned displayer 47, the user is to be cautioned by displaying the value obtained by detecting the accumulation of the driving electric power to the piezoelectric vibrator 3 using the integrating electric power meter 46. When the probe 6 is not found to be abnormal, the ordinary drive of the probe will be started.

FIGS. 7 to 10 show modifications of the probe in the ultrasonic aspirator of the present invention.

Figure 7:
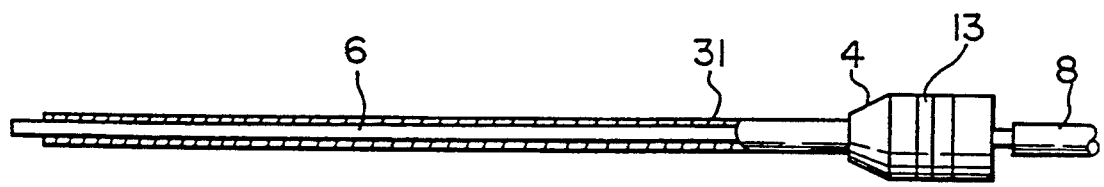
FIGS. 7 is side view showing modification of a probe.

In the modification shown in FIG. 7, the probe 6 is coated over the entire periphery with a protective tube 31 made, for example, of a polyimide resin which does not attenuate an ultrasonic vibration so that, when the probe 6 breaks, it will not drop into the body cavity from the sheath. The probe 6 may be coated on the inner periphery with this protective tube.

Figure 8A:
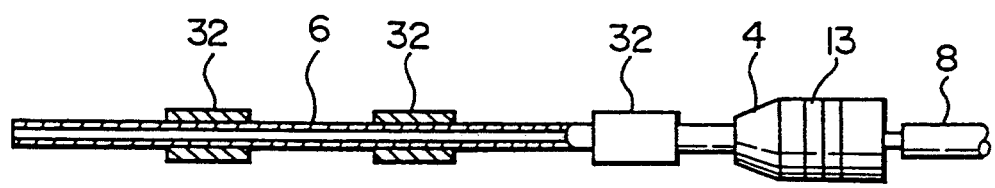
FIG. 8(A) is a side view showing another modification or a probe.
Figure 8B:
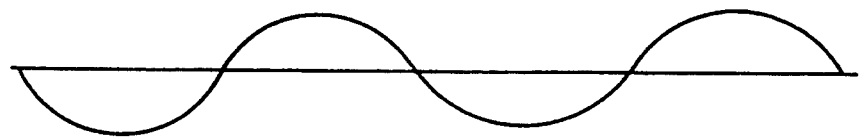
FIG. 8(B) shows the amplitude of an ultrasonic vibrator.

In the modification shown in FIG. 8(A) and 8(B), the probe 6 in the part in which the amplitude of the ultrasonic vibration is large, as shown in FIG. 8(B), is coated on the outer periphery or inner periphery with the same protective tube 32 as is shown in FIG. 7.

Figure 9:
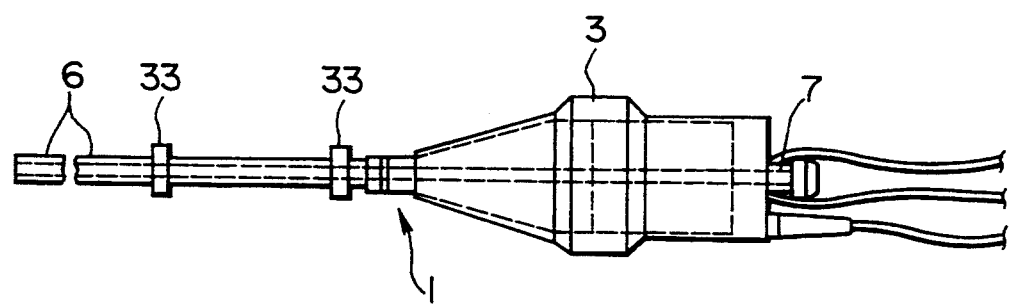
FIG. 9 is a side view of another modification or a probe.

In the modification shown in FIG. 9, a separate or integral flange 33 is formed on the outer periphery of the probe 6. A small diameter part, having an inside diameter smaller than the diameter of this flange 33, is formed near the tip opening on the sheath in which this probe 6 is inserted and assembled so that, even when the probe 6 breaks and tends to drop from the sheath, the flange 33 of the probe 6 will catch the small diameter part to prevent the probe from dropping.

Figure 10:
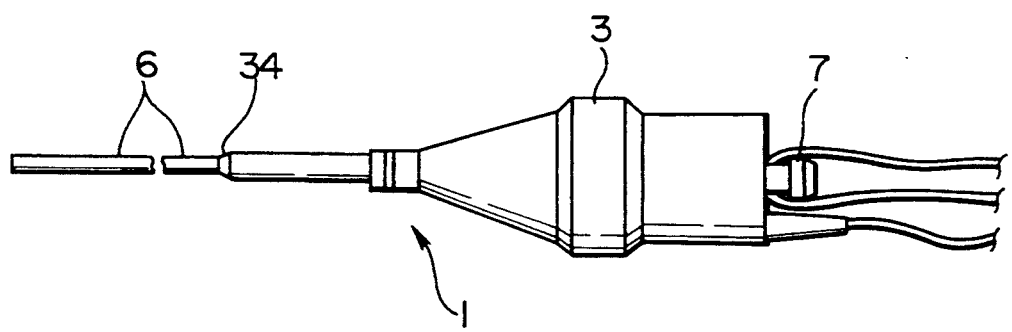
FIG. 10 is a side view of another modification of a probe.

In the modification shown in FIG. 10, a step 34 is formed on the probe 6 instead of providing a flange.

As explained above, according to the present invention, a break of a pipe-like probe transmits an ultrasonic vibration is detected and an ultrasonic oscillating drive is controlled by the detected signal so that, as soon as the probe breaks, the ultrasonic vibration will be stopped to prevent tissues within a body cavity from being hurt and to prevent broken pieces from dropping into the body cavity.

It is apparent that, in the present invention, a wide range of different working modes can be formed based on this invention without deviating from the spirit and scope of the invention. This invention is not restricted by its specific working modes except being limited by the appended claims.

What is claimed is:

1. An ultrasonic aspirator comprising:
   a probe, in a form of a pipe, as an ultrasonic vibration transmitting member provided on a base side with an ultrasonic vibrator which only transmits vibrations to a tip of said probe, said tip being used to contact a treated part which is an object tissue within a body cavity, said transmitted vibrations breaking the treated part into pieces, said probe further being provided with an inside path for aspirating the pieces of the treated part and for discharging the pieces outside the probe;
   an ultrasonic vibrator oscillating driving means for oscillating and for driving said ultrasonic vibrator;
   a probe break detecting means for detecting a break of said probe when said ultrasonic vibrator oscillating driving means operates, wherein said probe break detecting means includes a component which is enclosed within said probe; and
   an ultrasonic vibrator controlling means for stopping oscillation and drive of said ultrasonic vibrator by a detecting signal of said probe break detecting means.

2. An ultrasonic aspirator according to claim 1 wherein said probe is used as inserted and assembled in an endoscope.

3. An ultrasonic aspirator according to claim 1 wherein said ultrasonic vibrator oscillating driving means has an oscillator and a driving circuit.

4. An ultrasonic aspirator according to claim 3 wherein said ultrasonic vibrator controlling means switches an input current to the driving circuit on and off.

5. An ultrasonic aspirator according to claim 3 wherein said ultrasonic vibrator controlling means conducts and interrupts a high frequency signal input to said driving circuit from said oscillator.

6. An ultrasonic aspirator according to claim 1 wherein said probe break detecting means converts an ultrasonic echo reflected from said probe into an echo signal by applying an impulse to the ultrasonic vibrator of said probe and said probe break detecting means for detecting the echo signal.

7. An ultrasonic aspirator according to claim 1 wherein said probe break detecting means includes electrodes provided in an axial direction of said probe and said electrodes are broken by a break of said probe.

8. An ultrasonic aspirator according to claim 7 wherein said electrodes are wired in a pair in form of a U in the axial direction of the probe.

9. An ultrasonic aspirator according to claim 7 wherein said electrodes are wired in a plurality of pairs each in a form of a U in the axial direction over an entire periphery of said probe.

10. An ultrasonic aspirator according to claim 7 wherein said wired electrodes are in close contact with an outer periphery of said probe through an insulating layer and are also coated on surfaces with insulating layers.

11. An ultrasonic aspirator comprising:
a probe, in a form of a pipe, as an ultrasonic vibration transmitting member provided on a base side with an ultrasonic vibrator which only transmits vibrations to a tip of said probe, said tip being used to contact a treated part which is an object tissue within a body cavity, said transmitted vibrations breaking the treated part into pieces, said probe further being provided with an inside path for aspirating the pieces of the treated part and for discharging the pieces outside the probe;
an ultrasonic vibrator oscillating driving means for oscillating and for driving said ultrasonic vibrator;
a probe break detecting means for detecting a break of said probe by detecting a change in impedance characteristic during the vibration of said ultrasonic vibrator wherein said probe break detecting means includes a component which is enclosed within said probe; and
an ultrasonic vibrator controlling means for stopping oscillation and drive of said ultrasonic vibrator by a detecting signal of said probe break detecting means.

* * * * *